United States Patent [19]
Fukushima et al.

[11] 4,285,933
[45] Aug. 25, 1981

[54] PROCESS FOR CONCENTRATING BLOOD COAGULATION FACTOR XIII DERIVED FROM HUMAN PLACENTAE

[75] Inventors: Tunekazu Fukushima, Kobe; Satoshi Funakoshi, Katano, both of Japan

[73] Assignee: The Green Cross Corporation, Osaka, Japan

[21] Appl. No.: 91,245

[22] Filed: Nov. 2, 1979

[30] Foreign Application Priority Data

Nov. 7, 1978 [JP] Japan .............................. 53/136996

[51] Int. Cl.³ .............................................. A61K 35/48
[52] U.S. Cl. ..................................................... 424/105
[58] Field of Search ......................................... 424/105

[56] References Cited

U.S. PATENT DOCUMENTS 3,880,989  4/1975  Garcia ............................. 424/85 X

FOREIGN PATENT DOCUMENTS 53-59018  5/1978  Japan ..................................... 424/105

OTHER PUBLICATIONS

Pisano, Ann. N.Y. Acad. Sci., Zoz: 98 (1972).
McDonagh, 16th Int'l Cong. Hematol, Kyoto, (1976).
Mosher, J. Biol. Chem. 250:6614 (1975).

Primary Examiner—Frank Cacciapaglia, Jr.
Attorney, Agent, or Firm—Cushman, Darby & Cushman

[57] ABSTRACT

The invention relates to a process for concentrating blood coagulation Factor XIII (Fibrin stabilizing factor) which comprises removing a fraction precipitated at a pH of 6 to 9 in a concentration of 4 to 9% (W/V) of an alkylenoxide polymer or copolymer having a molecular weight of 2,000 to 20,000 from a crude globulin fraction obtained from human placentae by separating in albumin fraction therefrom, and then collecting the fraction precipitated in the concentration of 20 to 30% (W/V) of said polymer or copolymer, thereby obtaining easily said blood coagulation Factor XIII free from pyrogen in good yield.

1 Claim, No Drawings

PROCESS FOR CONCENTRATING BLOOD COAGULATION FACTOR XIII DERIVED FROM HUMAN PLACENTAE

This invention relates to a process for concentrating blood coagulation Factor XIII (Fibrin stabilizing factor, hereinafter referred to as Factor XIII) derived from human placentae.

Recently, much attention has been drawn to the clinical application of Factor XIII, which participates in the formation of insoluble fibrin on the fibrinogen-fibrin system, in the field of wound healing on the basis of the studies of the thrombus forming mechanism.

The abnormal symptom of bleeding and retarded healing of wounds observed in cases of congenital deficiency in Factor XIII has been known to be caused by incomplete formation of cross-linking between $\gamma$-chains of fibrins being the substrate of Factor XIII. Furthermore not only the cross-linking between $\gamma$-chains of fibrins, but also the biological significance of the cross-linking between $\alpha$-chains have attracted much interest. In other words, the cross-linking between $\gamma$-chains of fibrins regulates its chemical stability, whereas the said cross-linking between $\alpha$-chains regulates the physical and mechanical strengths of fibrins. Furthermore, it has been found that a cold insoluble globulin, which heretofore has been considered only as a contaminant always present at the time of purifying fibrinogen and antihemophilic factors, evidently plays a biologically important role as the substrate of Factor XIII like fibrin. In other words, according to the present view point, when a wound begins to heal, the primary phase of wound healing seems to be dependent on Factor XIII so that the cross-linking between $\alpha$-chains of fibrin develops among not only fibrins, but also among cold insoluble globulins. The following publications are added herein for reference.

(1) Pisano, J. J., "Ann. N.Y. Acad. Sci." 202, 98 (1972); (2) McDonagh R. P., "The 16th International Congr. Hematol, Kyoto." 1976; and (3) Mosher, D. F. "J. Biol. Chem." 250, 6614 (1975).

From the foregoing, it is evident that for clinical application, Factor XIII preparation is highly effective for a wide range of purposes, e.g. for remedying both congenital and aquired deficiency of Factor XIII as well as promoting general wound healing after surgery.

With regard to the raw materials for preparing Factor XIII, a human placenta is superior from the view point of price and yield and from the practical view point of the manufacturing a ready-made drugs.

Japanese Patent Kokai (Laid-Open) No. 59018/1978 disclosed that various studies were made on the developing of a process for producing Factor XIII and gave a solution to the problem of producing process connected with the production of ready-made drugs, such as albumin and $\gamma$-globulin, and found that Factor XIII is concentrated into a crude globulin fraction obtained in the step for producing albumin and $\gamma$-globulin from placentae, which step is mainly composed of ammonium sulfate fractionation method, and based on this finding, a process for producing Factor XIII was accomplished, and further a step for inactivating treatment of hepatitis virus, which is a common problem in blood products, was included in the process.

The process of said Japanese Patent Kokai (Laid-Open) No. 59018/1978 is outlined below.

(a) Mucoid protein is removed as a precipitate by centrifugation from placentae with a sodium chloride solution;

(b) the thus obtained supernatant liquor is brought to a condition of a ph of 5 to 7, ammonium sulfate saturation of 20 to 30% and at a temperature of 1° to 15° C. thereby removing a contained tissue protein as precipitate;

(c) the resulting supernatant is brought to a condition of a pH of 6 to 8 and an ammonium sulfate saturation of 45 to 55% to obtain a crude globulin fraction as precipitate and the resulting supernatant is utilized as a crude albumin fraction;

(d) acrinol is added to the said crude globulin fraction in an amount of 1-2% (W/V) and stands as it is for one night at a pH of 8.0 to 9.0 to separate $\gamma$-globulin and hemoglobin as precipitates;

(e) the resulting supernatant is filtrated and sodium chloride is added in a concentration of 2-8% (W/V) to the filtrate to remove the remaining acrinol, and after filtering out the precipitate, an absorbent selected from bentonite, active carbon, acid clay, etc. is added to the filtrate to remove the remaining acrinol;

(f) the obtained solution is filtered to remove precipitates, and ammonium sulfate is added to the solution in a concentration of 40 to 50% saturation and $\gamma$-globulin fraction is separated as precipitate, and as a supernatant, concentrated Factor XIII fraction is recovered;

(g) to the concentrated Factor XIII fraction, a stabilizer selected from the group consisting of neutral amino acid, monosaccharide, and sugar alcohol is added alone or in combination in a concentration of 10 to 20% (W/V), and then the solution is subjected to a heat treatment of 9 to 11 hours at 55° to 65° C. to induce the formation of heat unstable substances and an inactivation of the hepatitis virus;

(h) the heat-treated solution is then subjected to chromatographic treatment with an anion exchanger or a block electrophoresis to separate heat-unstable substances;

(i) finally, the obtained solution is dialyzed, sterilize-filtered and freeze-dried according to the known methods.

As seen from the above, the process disclosed in Japanese Patent Kokai (Laid-Open) No. 59018/1978 utilizes a number of steps to obtain Factor XIII after separating a crude globulin fraction and a crude albumin fraction by ammonium sulfate fractionation method. Accordingly, a contamination of pyrogen in the obtained Factor XIII has often been observed.

Upon making intensive studies on this point, it has now been found that an application of the polyalkyleneglycol precipitating fractionation method to the purification of the crude globulin fraction make possible a simplification of the steps and thereby enhancing the prevention of the contamination of pyrogen and furthermore bringing about an increase in yield. Moreover, the purity and stability of the obtained product according to the present invention are not different from those of the product of Japanese Patent Kokai (Laid-Open) No. 59018/1978.

According to the present invention, there is provided a process for concentrating Factor XIII derived from human placentae which comprises removing a fraction precipitated from a crude globulin fraction obtained from human placentae at a pH of 6 to 9 in a concentration of 4 to 9% (W/V) of alkyleneoxide polymer of copolymer having a molecular weight of 2,000 to 20,000, and then collecting a fraction precipitated at the same pH and in the concentration of 20 to 30% (W/V) of the abovementioned polymer or copolymer.

The present invention will be explained in detail in the following.

The crude globulin fraction derived from human placentae used in the process of the present invention is obtained from placentae extract solution produced according to a known method such as for example, disclosed in Japanese Patent Kokai (Laid-Open) No. 59018/1978. That is, foreign mucoid colloidal proteins are centrifugally removed from the extract solution of finely chopped human placentae using a saline solution. Then the supernatant is saturated with ammonium sulfate in a concentration of 20 to 30% at a temperature of 1° to 15° C. and at a pH of 5 to 7 to precipitate and remove tissue proteins. The resulting supernatant, which is a crude albumin fraction, is increased in its ammonium sulfate concentration to 45 to 55% solution at a pH of 6 to 8 to precipitate a fraction and then separate the fraction from the supernatant.

The obtained crude globulin fraction is subjected to a fractionation with an alkyleneoxide polymer or copolymer into a γ-globulin fraction, a hemoglobin fraction and a fraction containing a large amount of Factor XIII according to the method of the present invention.

More specifically, the crude globulin fraction obtained as precipitates in the above is dissolved in a buffer solution having a pH of 6 to 9, preferably 7, which contains preferably a divalent-metal chelating agent such as EDTA (ethylenediaminetetraaceticacid salt). To the obtained solution, is added alone or in combination an alkyleneoxide polymer or copolymer (referred to as polyol hereinafter) having a molecular weight of 2,000 to 20,000 such as polyoxyethylene or polyoxypropylene homopolymer or polyoxyethylene-polyoxypropylene copolymer (PLURONIC, polyol). To begin with, the polyol is dissolved in the solution in a concentration of 4 to 9% (W/V), preferably 7% (W/V), to form precipitates (γ-globulin fraction) which is centrifugally removed. To the obtained supernatant, the polyol is again added to make a final concentration of 20 to 30% (W/V), preferably 25% (W/V). The thus formed precipitate which is Factor XIII is collected by separating it from the supernatant (which is a hemoglobin fraction).

The desired concentrated Fraction XIII thus obtained is subjected, according to known method, to ion-exchange chromatography with DEAE-Sephadex, dialysis, sterilized filtration and freeze-drying to obtain a purified fraction which can be prepared into drugs.

However, it is desirable that the said purified fraction is subjected to heat-treatment before making preparations in medicine in order to inactivate hepatitis virus which may exist in the fraction. The inactivation method is the same to one as that disclosed in Japanese Patent Kokai (Laid-Open) No. 59018/1978. In other words, the inactivation is carried out by heating a buffer solution containing the said fraction having a pH of 6 to 9 at a temperature of 55° to 65° C. for 9 to 11 hours in the presence of a stabilizer such as a neutral amino acid, monosaccharide or sugar alcohol in a concentration of 10 to 20% (W/V). Heat unstable substances which are formed during the heat-treatment can be removed by means of chromatography with an anion exchanger such as DEAE-Sephadex or with block electrophoresis after cooling the hot solution. Thereafter, the fraction can be formed into drugs.

The drugs prepared from Factor XIII obtained as above contains 250 units in 4 ml, if the active amounts of Factor XIII contained in 1 ml of the normal fresh serum is fixed as one unit.

The present invention will be illustrated below by way of examples only for the purpose of illustration, but the invention is not limited to the contents of the embodiments shown in the examples and is to be construed only on the basis of the appended claim.

EXAMPLE 1

800 Milliliters of extract solution extracted from human placentae with normal saline solution (using about 840 placentae which weighed about 510 kilogram in total) was centrifugally separated. The pH of the filtrates was adjusted to 5.0 and the formed precipitates were separated. To the supernatant solution ammonium sulfate was added at a pH of 6 to a saturation of 25% to form precipitates which were centrifugally removed.

When ammonium sulfate was added to the obtained supernatant in a saturation of 70%, the precipitates of crude globulin fraction were formed. The fraction was collected by centrifugation.

3.5 Kilograms of the thus obtained crude globulin fraction was dissolved in 100 liters of 0.05 Mol phosphate buffer solution having a pH of 7.5 which contained 0.005 mol of EDTA. To the solution, 7.0 kg of PLURONIC (a copolymer of polyoxyethylene and polyoxypropylene having a mean molecular weight of 15,000) were added and dissolved therein. After standing the solution for one night as it was, the formed precipitates (which can be used for the purification of globulin) were removed by centrifugation. PLURONIC was again added to the obtained supernatant and increased in its concentration into a final concentration of 25% (W/V). After letting the solution stand as it was for one night, the formed precipitates were collected and dissolved in the same buffer solution as mentioned above. The solution was then subjected to heat-treatment of 60° C. for 10 hours, ion-exchange chromatography using DEAE-Sephadex, dialysis, sterilizing filtration and adjusting to dosage, followed by freeze-drying. 187 Grams of protein were obtained as products containing 2.2 milion units of the Factor XIII, if the activity of Factor XIII contained in 1 ml of normal human serum is fixed as one unit.

EXAMPLE 2

Now using 4.0 kilograms of polyoxypropylene having a mean molecular weight of 8,000 in place of the PLURONIC used in Example 1, globulin was removed therefrom, and then polyoxypropylene polymer was again added to the solution and its concentration was increased to a final concentration of 20% (W/V). The same purification methods as in Example 1 were repeated except for the above mentioned procedure. As a result, 151 grams of proteins which had a 1.8 million units of concentrated Factor XIII were obtained.

EXAMPLE 3

Using 9.0 kg of polyoxyethylene (mean molecular weight: 12,000) were used in place of the PLURONIC used in Example 1, globulin was removed at first. Thereafter, polyoxyethylene was again added and the concentration thereof was increased to a buffer concentration of 30% (W/V). Except for these procedures, the same purification methods as in Example 1 were adopted. As the results, 134 grams of protein which had 1.65 million units of concentrated Factor XIII were obtained.

The invention has succeeded in attaining the advantages whereby Factor XIII can be prepared from the by-product obtained in the course of manufacturing albumin and γ-globulin from human placentae without giving any disturbance to the course of preparing these substances the heat-treatment for inactivating hepatitis virus which is useful from the view point of the medical treatment can be administrated, and the contamination of pyrogen to the factor can be prevented by the shortening of the steps for its preparation. Furthermore, the concentrated Factor XIII having a high degree of safety and stability can be prepared in a high yield.

What is claimed is:

1. A process for concentrating a blood coagulation Factor XIII derived from human placentae consisting essentially of
   (1) recovering an extract with a physiologically saline solution from human placentae,
   (2) removing precipitate from the solution by centrifugation,
   (3) adding ammonium sulfate to the supernatant in a concentration of 20 to 30% (W/V),
   (4) recovering the supernatant and removing the precipitate therefrom,
   (5) adding ammonium sulfate to the supernatant in a concentration of 45 to 55% (W/V) to recover precipitate,
   (6) dissolving the precipitate into a phosphate buffer solution of pH 6 to 9 containing about 0.005 M of EDTA,
   (7) adding alkylene-oxide polymer of copolymer having a molecular weight of 2,000 to 20,000 which is selected from the group consisting of polyethylene oxide homopolymer, polypropylene oxide homopolymer and ethylene oxidepropylene oxide copolymer in a concentration of 4 to 0% W/V,
   (8) removing the formed precipitate and recovering the supernatant,
   (9) adding the above-mentioned alkylene-oxide polymer or copolymer to the supernatant in a concentration of 20 to 30% (W/V),
   (10) recovering the precipitate formed and dissolving it into a phosphate buffer of pH 6 to 9,
   (11) heat-treating the collected precipitate for 9 to 11 hours at 55° to 65° C. in an aqueous solution of a neutral amino acid, monosaccharide, sugar alcohol or a mixture of two or more thereof in a concentration of 10 to 20% (W/V) thereby to inactivate hepatitis virus,
   (12) contacting the resulting solution with a DEAE-crosslinked dextran which had been equilibrated to pH of 6 to 9 thereby to absorb blood coagulation Factor XIII,
   (13) eluting the blood coagulation Factor XIII with an about 0.05 M phosphate buffer containing about 0.5 M NaCl,
   (14) subjecting the collected eluate to dialysis, sterilizing filtration and freeze-drying.